(12) United States Patent
Keem

(10) Patent No.: US 11,399,959 B2
(45) Date of Patent: Aug. 2, 2022

(54) EXPANDABLE LUMBAR CAGE AND METHOD FOR INSERTING THE SAME

(71) Applicant: HILO INNOVATIONS, LLC, Wilmington, DE (US)

(72) Inventor: Sean Kyong-Ho Keem, Seattle, WA (US)

(73) Assignee: HILO INNOVATIONS, LLC, Wilmington, DE (US)

( * ) Notice: Subject to any disclaimer, the term of this patent is extended or adjusted under 35 U.S.C. 154(b) by 0 days.

(21) Appl. No.: 17/424,878

(22) PCT Filed: Dec. 24, 2020

(86) PCT No.: PCT/IB2020/062428
§ 371 (c)(1),
(2) Date: Jul. 21, 2021

(87) PCT Pub. No.: WO2021/234443
PCT Pub. Date: Nov. 25, 2021

(65) Prior Publication Data
US 2022/0117748 A1    Apr. 21, 2022

(30) Foreign Application Priority Data

May 22, 2020 (KR) .......................... 10-2020-0061433
Dec. 8, 2020 (KR) .......................... 10-2020-0170829

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/3054* (2013.01); *A61F 2002/30433* (2013.01); *A61F 2002/30579* (2013.01)

(58) Field of Classification Search
CPC .......... A61F 2/447; A61F 2/44; A61F 2/4611; A61F 2002/3054; A61F 2002/30579
USPC ....................... 623/17.11–17.16; 606/99–100
See application file for complete search history.

(56) References Cited

U.S. PATENT DOCUMENTS

| | | | |
|---|---|---|---|
| 9,750,618 B1 | 9/2017 | Daffinson et al. | |
| 9,820,865 B2 | 11/2017 | Sharabani et al. | |
| 10,022,239 B1 | 7/2018 | Lentner et al. | |
| 10,575,966 B2 | 3/2020 | Logan et al. | |
| 10,786,367 B2 * | 9/2020 | Sharabani ............... | A61F 2/447 623/17.16 |
| 2015/0190242 A1 * | 7/2015 | Blain ...................... | A61F 2/447 623/17.12 |
| 2015/0272743 A1 | 10/2015 | Jimenez et al. | |

(Continued)

FOREIGN PATENT DOCUMENTS

JP   2016-538953 A   12/2016
KR   10-1352820 B1   1/2014

*Primary Examiner* — Jessica Weiss
(74) *Attorney, Agent, or Firm* — Novick, Kim & Lee, PLLC; Sang Ho Lee; Hyun Woo Shin

(57) ABSTRACT

Provided is an expandable lumbar cage including an upper member, a lower member, a sagittal adjustment unit to adjust sagittal balance of a spine, and a coronal adjustment unit to adjust coronal balance of the spine. According to the foregoing description, it is possible to simultaneously adjust the sagittal balance of the spine as well as the coronal balance, thereby achieving effective treatment of the spine having compound deformity.

15 Claims, 13 Drawing Sheets

(56) References Cited

U.S. PATENT DOCUMENTS

| | | | |
|---|---|---|---|
| 2016/0250034 A1* | 9/2016 | Loebl | A61F 2/4611 |
| | | | 623/17.16 |
| 2019/0000646 A1* | 1/2019 | Daffinson | A61F 2/4611 |
| | | | 623/17.16 |
| 2019/0008649 A1* | 1/2019 | Logan | A61F 2/447 |
| | | | 623/17.16 |
| 2019/0133779 A1 | 5/2019 | McLaughlin et al. | |
| 2020/0008951 A1* | 1/2020 | McClintock | A61F 2/442 |
| | | | 623/17.16 |
| 2020/0129307 A1* | 4/2020 | Hunziker | A61F 2/4455 |
| | | | 623/17.16 |
| 2020/0383797 A1* | 12/2020 | Predick | A61F 2/30 |
| | | | 623/17.16 |

* cited by examiner

EXPANDABLE LUMBAR CAGE AND METHOD FOR INSERTING THE SAME

TECHNICAL FIELD

The present disclosure relates to an expandable lumbar cage and an expandable cage insertion method using the same, and more particularly, to an expandable lumbar cage for restoring the function of the spine by providing the intervertebral gap in place of a damaged disc between vertebrae to treat a spinal disc related disease and a method for inserting the same.

BACKGROUND ART

In general, discs positioned between vertebrae serve as cushions to absorb loads and impacts of the body. Discs distribute impacts like springs, as well as hold the vertebrae not to move out of place, separate two vertebrae to prevent nerve compression in the neuroforamina in motion, and help each vertebra to move smoothly.

Meanwhile, when external artificial factors, degeneration, or abnormal posture last long in the disc, as the intervertebral gap gradually become narrower or the vertebra descends, various adverse effects such as spinal deformity may occur.

One method for treating diseases caused by the disc is fusion, which includes removing a damaged intervertebral disc and inserting a prosthesis, also known as a cage, into a space between two adjacent vertebrae to replace the disc. In this instance, the cage serves to return the distance between the vertebrae to the original state to restore the function of the spine.

Korean Patent No. 10-1352820 as an example of technology for the cage discloses an expandable intervertebral cage comprising a cage body including an upper support unit to support the upper vertebra, a lower support unit to support the lower vertebra, and a connection unit to connect the ends of the upper support unit and the lower support unit; and a sliding member to increase or decrease the distance between the upper support unit and the lower support unit by the sliding movement between the upper support unit and the lower support unit, wherein the sliding member further includes a press bolt screw-coupled to the sliding member to allow the sliding movement of the sliding member by the screw coupling.

Meanwhile, spinal deformity rarely occurs in a single plane such as scoliosis alone and kyphosis alone, and is usually in three dimensions, and most of spinal deformity is compound deformity of combined scoliosis and kyphosis.

However, the conventional expandable lumbar cage is designed to adjust only one of the sagittal balance of the spine or the coronal balance of the spine, so when most of spinal deformity is compound, the conventional cage has the limited treatment effect and there are limitations in treating the spine having compound deformity. Additionally, since the conventional expandable lumbar cage is inserted by the posterior approach, there is a risk of damage to the muscles or ligaments of the human body during the insertion, which can increase the burden of treatment.

RELATED LITERATURES

Patent Literatures (Patent Literature 0001) Korean Patent No. 10-1352820

DISCLOSURE

Technical Problem

The present disclosure is directed to providing an expandable lumbar cage configured to simultaneously corrects both the sagittal balance and the coronal balance of the spine, thereby effectively treating complex deformities in the spine using only one expandable cage, and a method for inserting the same.

The present disclosure is further directed to providing an expandable lumbar cage that can be inserted with a lateral approach (trans-psoas approach) or an anterolateral approach (ante-psoas approach), which minimizes the post-surgery pain caused by incisions of muscles or ligaments for the posterior or posterolateral approach, and a method for inserting the same.

Technical Solution

According to an aspect of the present disclosure, the present disclosure provides an expandable lumbar cage including an upper member, a lower member spaced apart below the upper member, a sagittal adjustment unit disposed between the upper member and the lower member, to adjust a distance between the upper member and the lower member, thereby adjusting sagittal balance of a spine, and a coronal adjustment unit disposed between the upper member and the lower member and coupled to one side of each of the upper member and the lower member, to move up and down one side of each of the upper member and the lower member to adjust inclination of the upper member and the lower member, thereby adjusting coronal balance of the spine.

The sagittal adjustment unit may include a height adjustment screw positioned along a lengthwise direction of the upper member and the lower member, and having a screw thread on an outer peripheral surface, wherein an adjustment instrument is inserted into the height adjustment screw, and the height adjustment screw rotates with rotation of the adjustment instrument, a height adjustment member screw-coupled to the height adjustment screw to move with the rotation of the height adjustment screw, with top in contact with a lower surface of the upper member and bottom in contact with an upper surface of the lower member, wherein the height adjustment member adjusts the distance between the upper member and the lower member by the movement, and a support connection unit with one side connected to the height adjustment member and the other side connected to each of the upper member and the lower member to support the height adjustment member.

The height adjustment member may include an adjustment unit which moves by the rotation of the height adjustment screw screw-coupled to the adjustment unit through a screw coupling hole, with top in contact with the lower surface of the upper member and bottom in contact with the upper surface of the lower member, wherein the adjustment unit moves up and down the upper member and the lower member with the movement, a support unit disposed on the other side of the upper member and the lower member to support the upper member and the lower member, and a connection unit connecting the adjustment unit to the support unit.

The adjustment unit may include a first sliding surface which is formed with inclination, comes into contact with an upper slope surface formed on the lower surface of the upper member and makes a sliding movement along the upper slope surface during movement, and a second sliding surface which is formed with inclination, comes into contact with a lower slope surface formed on the upper surface of the lower member and makes a sliding movement along the lower slope surface during movement, and the adjustment unit may be configured to move up and down the upper member and the lower member along the first sliding surface and the second sliding surface with the movement, to reduce or expand the distance between the upper member and the lower member.

The adjustment unit may be formed with each of the first sliding surface and the second sliding surface at a same slope angle with respect to a movement direction.

The adjustment unit may have the first sliding surface and the second sliding surface symmetrically disposed in a vertical direction, become narrower as it goes inward of the upper member and the lower member, and be configured to expand the distance between the upper member and the lower member as it moves inward.

The upper member may have a first slope surface upward sloping outwards on a lower surface of the other side end, the lower member may have a second slope surface downward sloping outwards on an upper surface of the other side end opposite the first slope surface, and the support unit may have a first slope support surface in contact with the first slope surface, and a second slope support surface in contact with the second slope surface.

The support unit may have an insertion hole into which the adjustment instrument is inserted, and the insertion hole may be coaxial with the screw coupling hole.

The support connection unit may include a connection axis coupled to the support unit, a first support link with one side pivotably coupled to the connection axis and the other side pivotably coupled to the upper member, and a second support link with one side pivotably coupled to the connection axis and the other side pivotably coupled to the lower member.

The upper member may be formed with a rectangular plan shape, and may have an upper surface sloping downward from anterior to posterior of the spine with respect to a sagittal plane of the spine.

The lower member may be formed with a rectangular plan shape corresponding to the plan shape of the upper member, and may have a lower surface sloping upward from anterior to posterior of the spine with respect to the sagittal plane of the spine.

The coronal adjustment unit may include a slope adjustment screw positioned along a lengthwise direction of the upper member and the lower member, and having a screw thread on an outer peripheral surface, wherein the adjustment instrument is inserted into the slope adjustment screw, and the slope adjustment screw rotates with rotation of the adjustment instrument, a movement member formed in a tubular shape having a screw thread on an inner peripheral surface into which the slope adjustment screw is screw-coupled, wherein the movement member moves with the rotation of the slope adjustment screw, and a slope adjustment unit with one side connected to the movement member, and the other side connected to each of the upper member and the lower member, to move up and down one side of the upper member and the lower member with the movement of the movement member.

The slope adjustment unit may include a pivot axis coupled to the movement member, an upper link with one side pivotably coupled to the pivot axis and the other side coupled to one side of the upper member, and a lower link with one side pivotably coupled to the pivot axis and the other side coupled to one side of the lower member.

The expandable lumbar cage may further include a guide unit disposed between the upper member and the lower member, and including a seating unit in which an end of the height adjustment screw and an end of the slope adjustment screw disposed opposite the end of the height adjustment screw are seated, to guide the height adjustment screw and the slope adjustment screw.

The height adjustment screw, into which the adjustment instrument is inserted, may rotate by the rotation of the adjustment instrument, and may have a first adjustment hole having a polygonal cross-sectional shape, and the slope adjustment screw, into which the adjustment instrument is inserted, may rotate by the rotation of the adjustment instrument, and may have a second adjustment hole having a same diameter and cross-sectional shape as the first adjustment hole.

The height adjustment screw and the slope adjustment screw may be aligned such that the first adjustment hole and the second adjustment hole are coaxially arranged, and the adjustment instrument may be configured to rotate at least one of the height adjustment screw or the slope adjustment screw according to an insertion depth.

According to another aspect of the present disclosure, the present disclosure provides a method for inserting an expandable lumbar cage including inserting the expandable lumbar cage into an implantation space, the expandable lumbar cage including an upper member, a lower member spaced apart below the upper member, a sagittal adjustment unit disposed between the upper member and the lower member, to adjust a distance between the upper member and the lower member, thereby adjusting sagittal balance of a spine, and a coronal adjustment unit disposed between the upper member and the lower member to adjust inclination of the upper member and the lower member, thereby adjusting coronal balance of the spine, adjusting the sagittal balance of the spine by expanding the distance between the upper member and the lower member with respect to a sagittal plane of the spine through the sagittal adjustment unit, and adjusting the coronal balance of the spine by expanding the upper member and the lower member with inclination on one side with respect to a coronal plane of the spine through the coronal adjustment unit.

Inserting the expandable lumbar cage into the implantation space may include inserting the expandable lumbar cage in a lateral position or anterolateral position of the spine.

The sagittal adjustment unit and the coronal adjustment unit may be respectively configured to adjust the sagittal balance and the coronal balance of the spine by a height adjustment screw and a slope adjustment screw which are coaxially aligned and rotated by an adjustment instrument, and adjusting the sagittal balance and the coronal balance may include inserting the adjustment instrument using the height adjustment screw of one side of the expandable lumbar cage or the slope adjustment screw of the other side of the expandable lumbar cage, and rotating at least one of the height adjustment screw or the slope adjustment screw according to an insertion depth of the adjustment instrument with respect to the expandable lumbar cage to adjust the sagittal balance and the coronal balance.

An upper surface of the upper member and a lower surface of the lower member may be inclined with respect to the sagittal plane of the spine so that a height of one side of the expandable lumbar cage is higher than a height of the other side with respect to the sagittal plane of the spine, and inserting the expandable lumbar cage into the implantation space may include placing the expandable lumbar cage such that one side of the expandable lumbar cage faces an anterior portion of the spine and inserting into the implantation space.

Advantageous Effects

The expandable lumbar cage according to the present disclosure and a method for inserting the same provide the following effects.

First, it is possible to treat scoliosis or kyphosis by adjusting not only the sagittal balance of the spine but also the coronal balance of the spine through the sagittal adjustment unit and the coronal adjustment unit, and effectively treat compound spinal deformity using one configuration.

Second, the insertion in the lateral or anterolateral position of the spine minimizes the risk of damage to the muscles or ligaments of the human body during surgery, thereby ensuring safer surgery, and it is possible to achieve not only lateral lumbar interbody fusion (LLIF) but also Anteropsoas (Anterolateral) Interbody Fusion.

Third, a user can operate the sagittal adjustment unit and the coronal adjustment unit with one adjustment instrument, thereby allowing the user to efficiently perform the task of adjusting the sagittal balance and the coronal balance.

Fourth, due to the anterior-posterior symmetry with respect to the lengthwise direction (insertion direction), when adjusting the coronal balance through the coronal adjustment unit, it is possible to easily change the expansion location by changing the anterior-posterior direction according to the expansion location for each of the left side and the right left of the spine, thereby minimizing the incision site.

Fifth, it is possible to adjust the sagittal balance and the coronal balance by utilizing the screw thread pitch and through the rotation of the height adjustment screw of the sagittal adjustment unit and the slope adjustment screw of the coronal adjustment unit, thereby achieving precise expansion adjustments by means of the screw thread pitch and obtaining optimal treatment for the spine condition, and the adjustment can be performed by the simple rotation of the height adjustment screw and the slope adjustment screw, thereby improving the usability.

BEST MODE

Figure 1:
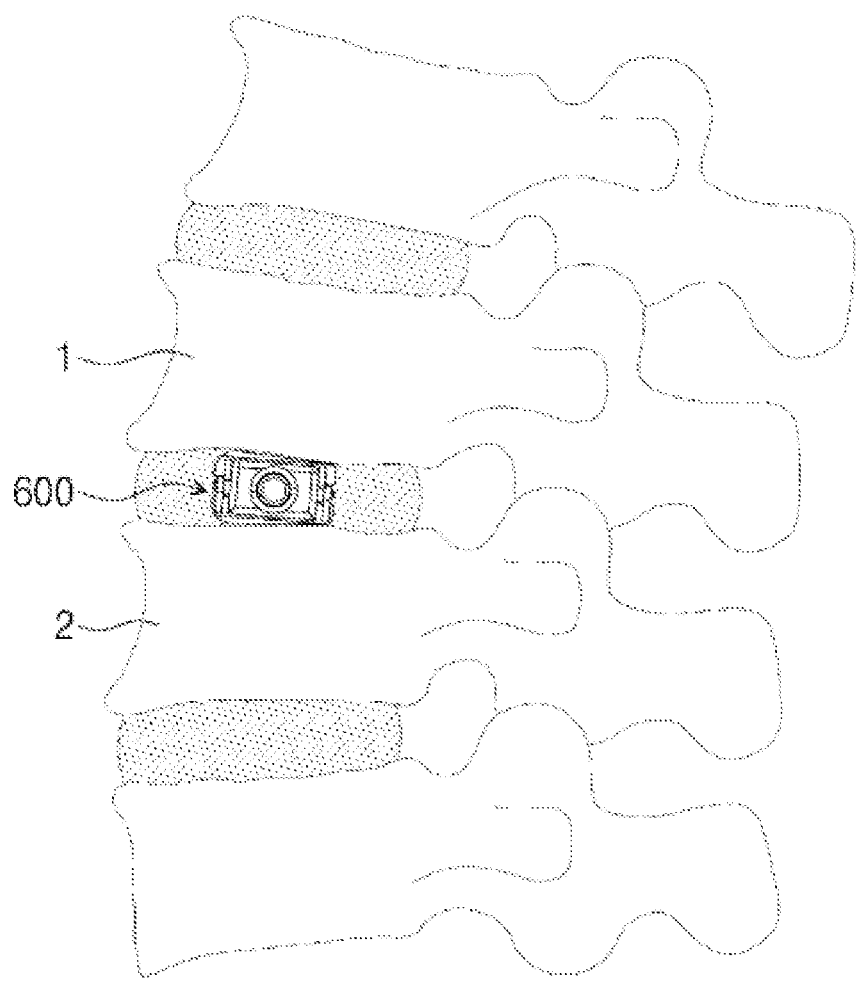
FIG. 1 is a diagram showing an expandable lumbar cage according to an embodiment of the present disclosure inserted into the spine when viewed from a sagittal plane.

Hereinafter, the preferred embodiments of the present disclosure will be described in detail with reference to the accompanying drawings.

The terms as used herein are general terms selected as those being now used as widely as possible in consideration of functions in the present disclosure, but they may vary depending on the intention of those skilled in the art or the convention or the emergence of new technology. Additionally, in certain cases, there may be terms arbitrarily selected by the applicant, and in this case, the meaning will be described in the corresponding description part of the specification. Accordingly, the terms as used herein should be defined based on the meaning of the terms and the context throughout the specification, rather than simply the name of the terms. Unless expressly stated to the contrary, the term "comprises" when used in this specification, specifies the presence of stated elements, but does not preclude the presence or addition of one or more other elements. Additionally, the term "unit" as used herein refers to a processing unit of at least one function or operation, and in the specification, a "user" may be not only a medical expert who works at a hospital, such as a doctor, a medical technologist and a radiographer but also an emergency medical technician who handles medical equipment, but is not limited thereto. A "subject" may include not only a patient who needs treatment but also an animal for use in the veterinary applications.

The embodiments of the present disclosure will be described in sufficiently detail with reference to the accompanying drawings to allow those skilled in the art to easily practice the present disclosure. However, the present disclosure may be embodied in many other forms and is not limited to the disclosed embodiments. Additionally, for clarity, some illustrations irrelevant to the description are omitted in the drawings, and like reference signs are affixed to like elements throughout the specification.

First, when a disc is damaged, the damaged disc is removed, and an expandable lumbar cage 600 according to an embodiment of the present disclosure (hereinafter referred to as an 'expandable cage') is inserted into an implantation space between an upper vertebra 1 and a lower vertebra 2 in place of the removed disc to provide an intervertebral gap. The expandable lumbar cage 600 is configured to simultaneously adjust not only the sagittal balance of the spine but also the coronal balance of the spine, thereby effectively treating complex deformity of the spine.

Hereinafter, the expandable cage according to an embodiment of the present disclosure will be described with reference to the drawings.

FIG. 1 shows the expandable cage 600 according to an embodiment of the present disclosure inserted into the spine when viewed from a sagittal plane. Referring to the drawing, as shown, the expandable cage 600 of the present disclosure may be configured to adjust the sagittal balance of the spine by expansion in a direction (vertical direction) perpendicular to the sagittal plane of the spine.

Figure 2:
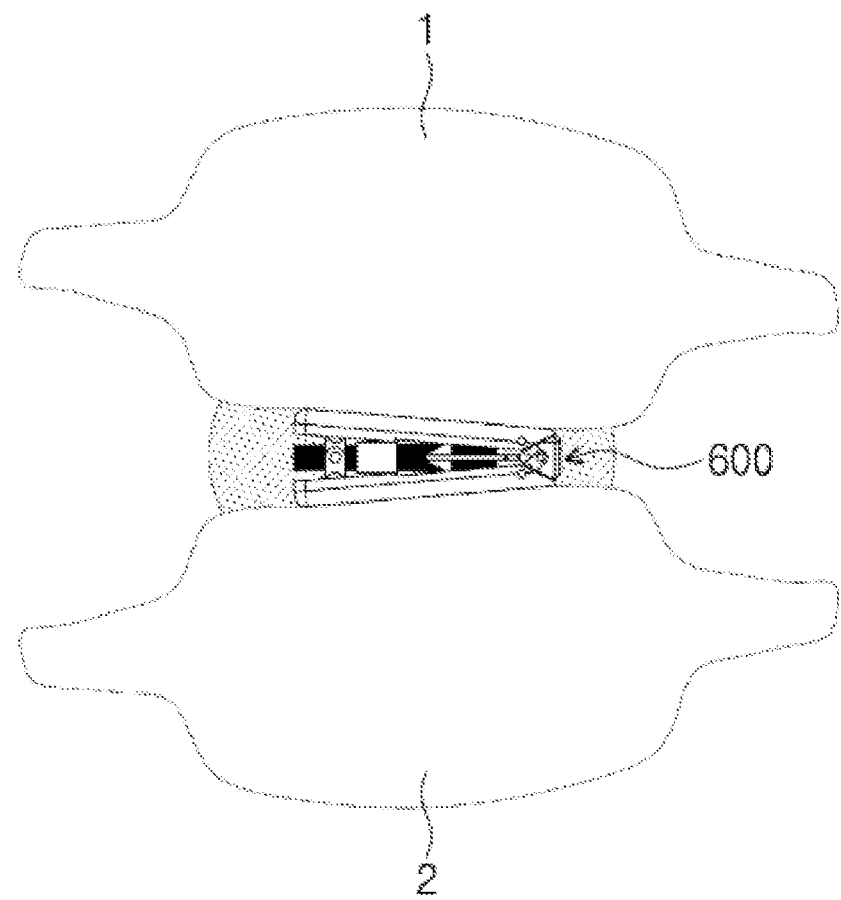
FIG. 2 is a diagram showing an expandable lumbar cage according to an embodiment of the present disclosure inserted into the spine when viewed from a coronal plane.

FIG. 2 shows the expandable cage 600 inserted into the spine when viewed from a coronal plane. Referring to the drawing, as shown, in addition to the expansion in the direction perpendicular to the sagittal plane of the spine, the expandable cage 600 of the present disclosure may be configured to adjust the coronal balance of the spine by expansion on one side (left side in the drawing) in a direction (vertical direction) perpendicular to the coronal plane of the spine. Here, although the drawing shows the expandable cage 600 expanded on the left side of the spine, this is an embodiment and the expandable cage 600 may be expanded at a different location, for example, on the other side (right side in the drawing) and thus may be selectively expanded on the left side and the right side of the spine.

Hereinafter, the expandable cage 600 of the present disclosure capable of adjusting the sagittal balance and coronal balance will be described in detail with reference to FIGS. 3 to 10.

Figure 3:
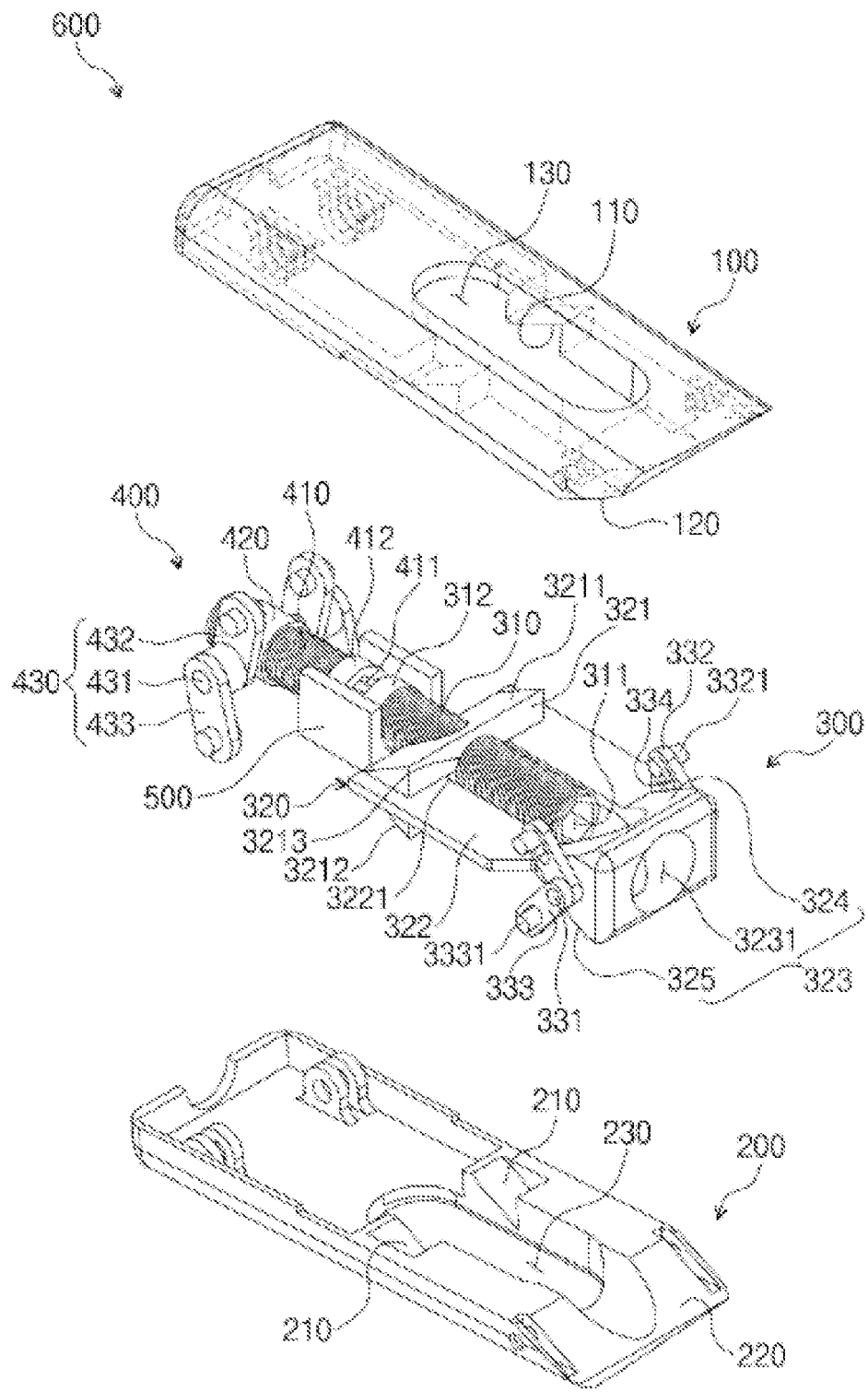
FIG. 3 is an exploded perspective view of an expandable lumbar cage according to an embodiment of the present disclosure.
Figure 4:
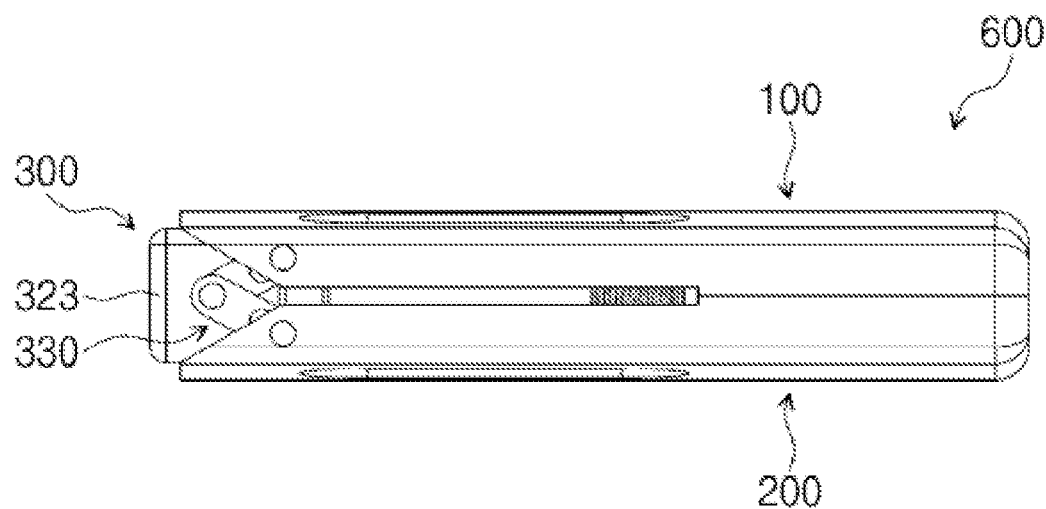
FIG. 4 is a front view showing an expandable lumbar cage according to an embodiment of the present disclosure.
Figure 5:
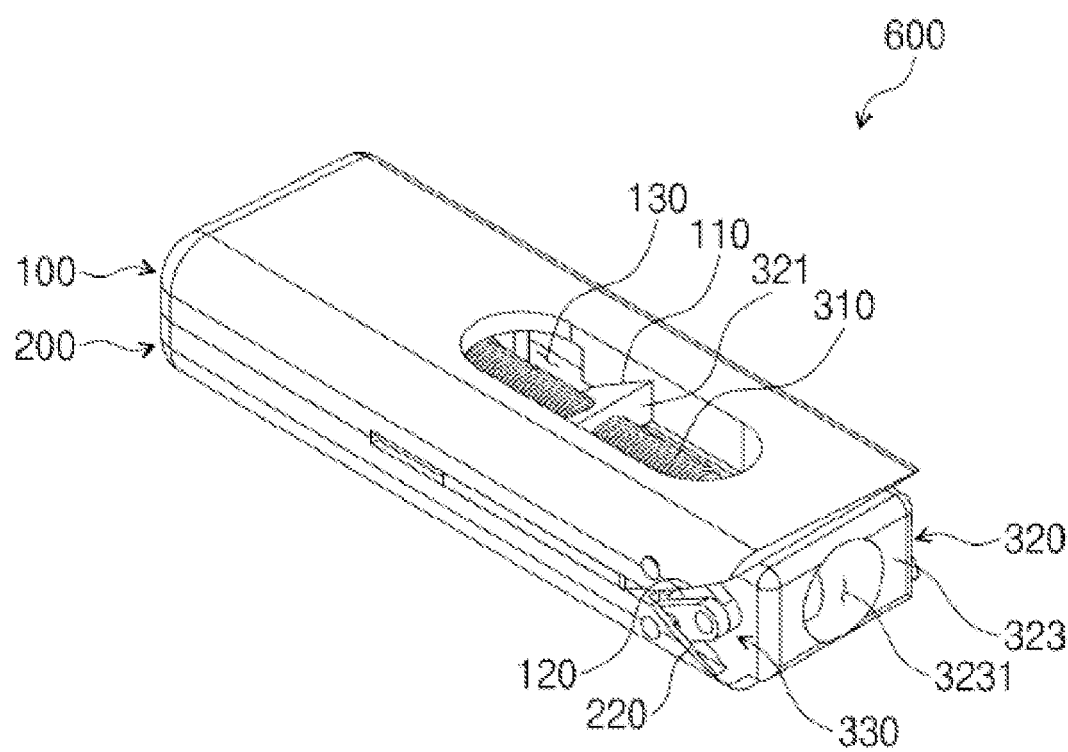
FIG. 5 is a perspective view showing the expandable lumbar cage of FIG. 4.
Figure 6:
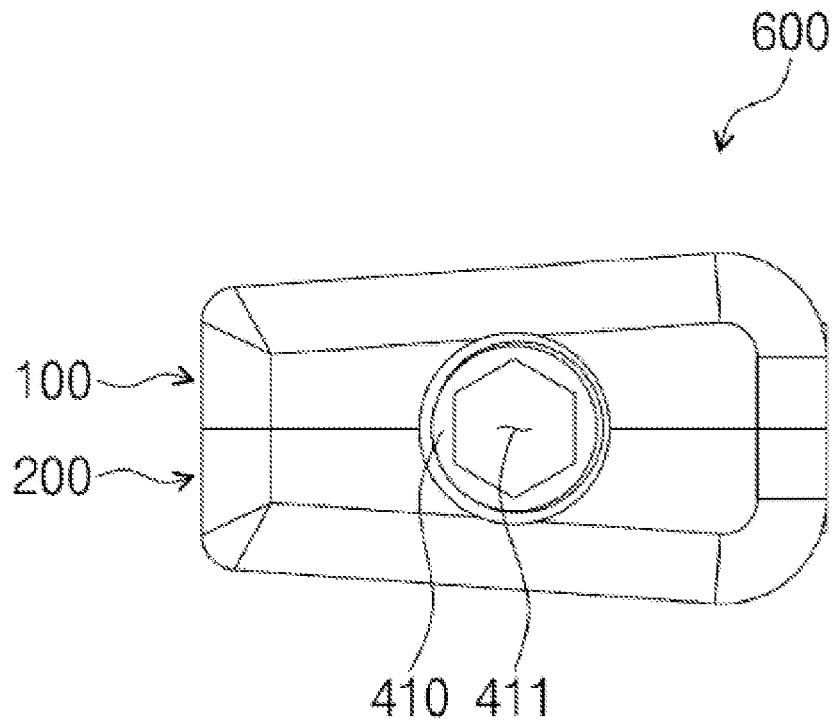
FIG. 6 is a side view showing the expandable lumbar cage of FIG. 4.
Figure 7:
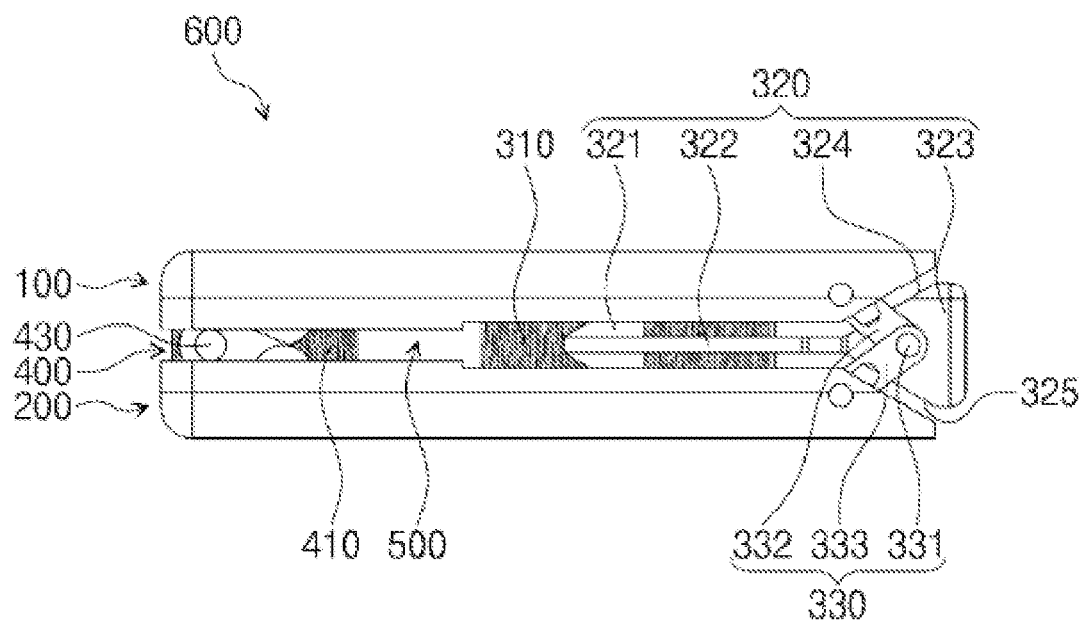
FIG. 7 is a front view showing an expandable lumbar cage according to an embodiment of the present disclosure, expanded in the vertical direction by a sagittal adjustment unit.
Figure 8:
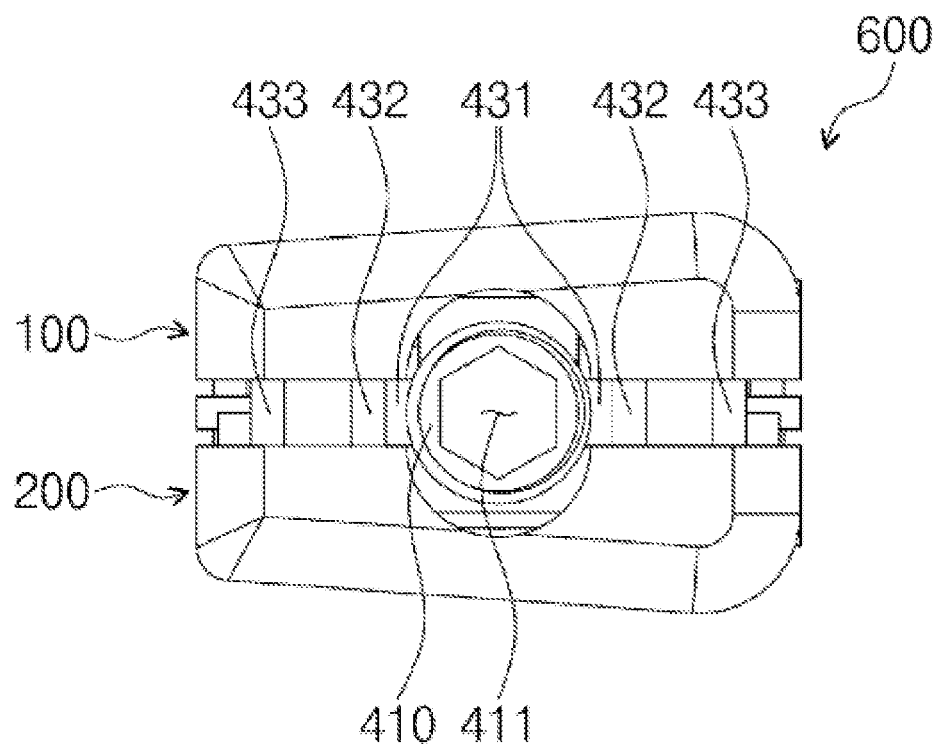
FIG. 8 is a side view of an expandable lumbar cage expanded by the sagittal adjustment unit of FIG. 7.
Figure 9:
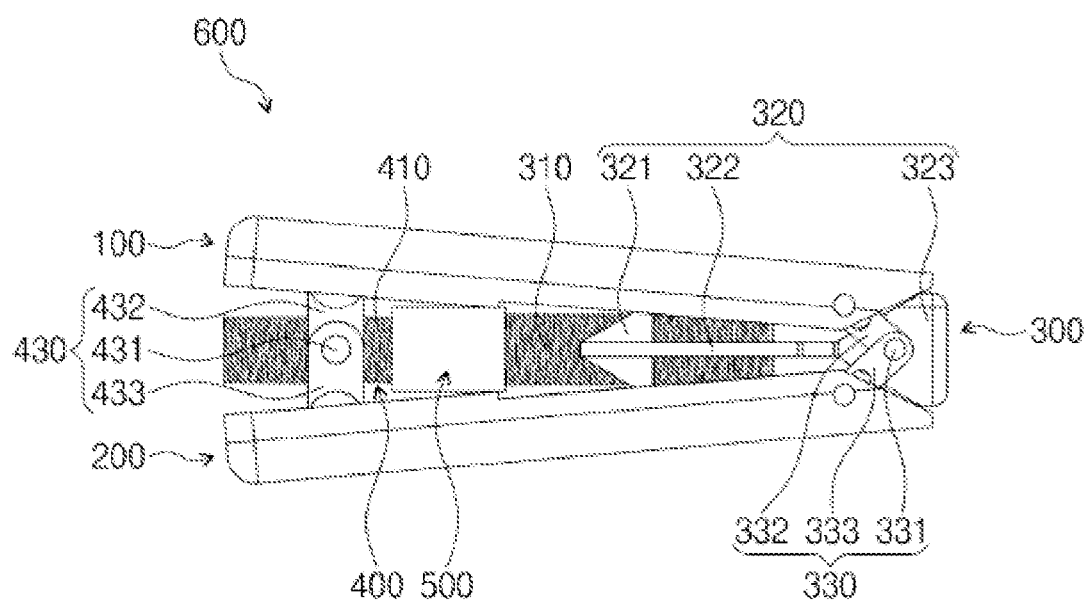
FIG. 9 is a front view showing the expandable lumbar cage of FIG. 7, expanded on one side in the vertical direction by a coronal adjustment unit.
Figure 10:
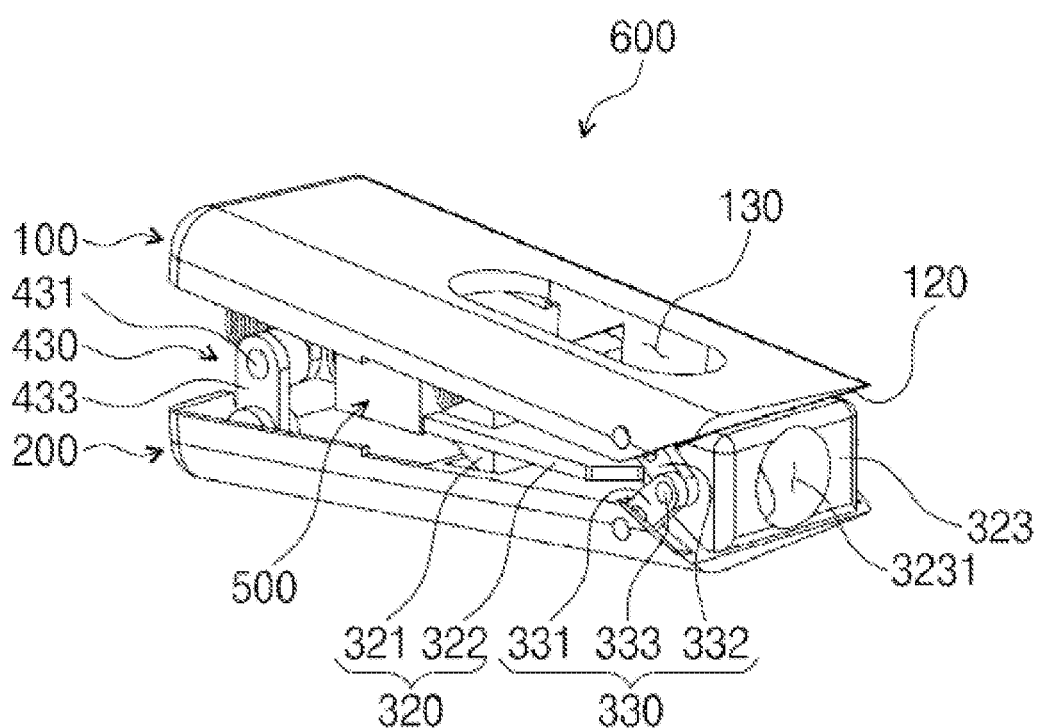
FIG. 10 is a perspective view showing the expandable lumbar cage of FIG. 9.

First, FIG. 3 is an exploded perspective view showing the configuration of the expandable cage 600 of the present disclosure. FIGS. 4 to 6 are diagrams showing the expandable cage 600 in a non-expanded state, and FIGS. 7 to 10 are diagrams showing the expandable cage 600 in an expanded state.

Referring to FIGS. 3 to 6, the expandable cage 600 of the present disclosure may include an upper member 100, a lower member 200, a sagittal adjustment unit 300 and a coronal adjustment unit 400.

First, the upper member 100 may have a rectangular plan shape, considering the implantation space and the shape and size of the disc, and may be formed in the shape of a plate having a set thickness (height). Preferably, the upper member 100 may be formed in the range of 18-22 mm in width, 45-55 mm in length and 8-16 mm in height, but when the subject is an adult, it is a desirable size considering the average implantation space, and is not limited thereto.

Meanwhile, the top of the upper member 100 is coupled and fixed to the upper vertebra 1. To this end, the upper member 100 may have a flat upper surface, and although not shown, may be fixed with the upper vertebra 1 through a fixing means.

Here, for fixing with the upper vertebra 1, the fixing means may include a wedge type fixing protrusion (spike) projected from the upper surface of the upper member 100, a porous surface to facilitate the bone growth or a fixing pin. Additionally, the fixing means may be integrally formed with the upper member 100 so that the fixing means and the upper member 100 may be made as one product in the manufacture, and a variety of configurations may be applied if the upper member 100 and the upper vertebra 1 are fixed to each other.

The lower member 200 may have a rectangular plan shape to match the plan shape of the upper member 100, and may be formed in the shape of a plate having a set thickness (height). The lower member 200 may be formed in the range of 18-22 mm in width, 45-55 mm in length and 8-16 mm in height to match the upper member 100, but is not limited thereto.

The lower member 200 may be spaced apart from the upper member 100 and may have a flat lower surface, and the bottom may be fixed to the lower vertebra 2 through the above-described fixing means.

Meanwhile, the upper member 100 and the lower member 200 connected to each other are preferably formed in a wedge shape with respect to the sagittal plane.

In detail, in a healthy person's spine, to efficiently distribute the force of gravity vertically applied to the spinal column, the cervical vertebrae curve forward (cervical lordosis), the thoracic vertebrae curve backward (thoracic kyphosis), and the lumbar vertebrae curve forward again (lumbar lordosis), overall forming an S-shaped curve when viewed from the side (the sagittal plane).

Meanwhile, the human spine is made of 26 bones, the lumbar vertebrae consist of 5 bones, and 5 discs lie between each vertebra to absorb impacts. In this instance, each disc is compressed such that the lumbar vertebrae curve forward, and especially, in the case of the lumbar vertebrae, since most of the center of gravity lies in the posterior portion, higher loads act on the posterior portion and compress in a wedge shape, and accordingly the discs have a corresponding wedge shape.

Accordingly, the expandable cage 600 of the present disclosure is preferably formed in a wedge shape with respect to the sagittal plane to conform to the disc shape.

The upper member 100 may have the upper surface sloping gradually downward from anterior to posterior of the spine with respect to the sagittal plane of the spine. Additionally, the lower member 200 may have the lower surface sloping gradually upward from anterior to posterior of the spine with respect to the sagittal plane of the spine.

Further, the upper surface of the upper member 100 and the lower surface of the lower member 200 may be symmetrically formed with respect to the sagittal plane, and the slope of each surface relative to the horizontal plane may be formed at the same angle in the range of 8° to 10°.

Considering that when a healthy person's spine is viewed from the side, the cervical vertebrae and the thoracic vertebrae have the curved angle ranging from 20° to 40°, and the lumbar vertebrae have the curved angle ranging from 30° to 50°. In the case of the lumbar vertebrae (including the first lumbar vertebra) consisting of 5 discs, when the 5 discs form the wedge angle of 30° to 50° together, the disc angle of one segment may be 8° to 10°. In other words, all the 5 discs of the lumbar vertebrae do not form the same angle, but except the lowest disc, the angle of each disc is almost similar, and by this reason, when it is assumed that 5 discs form the angle of the lumbar vertebrae in the range of 30° to 50° together, one disc angle may range between 8° and 10°.

The upper member 100 may have a first slope surface 120 upward sloping outwards on the lower surface of the other side end. Additionally, the lower member 200 may have a second slope surface 220 downward sloping outwards on the upper surface of the other side end opposite the first slope surface 120. Here, the first slope surface 120 and the second slope surface 220 are formed to match the shape of a first slope support surface 324 and a second slope support surface 325 of a support unit 323 described below, to reduce interference caused by the movement of the support unit 323.

The expandable cage 600 is formed in a cuboidal shape in anterior-posterior symmetry with respect to the insertion direction, and thus the expansion location for coronal balance adjustment may be switched by changing the anterior-posterior direction when inserting. That is, the expandable cage 600 may expand for each of the left side and the right side of the spine only by the direction change, thereby minimizing the incision site.

The expandable cage 600 may have a long upper through-hole 130 formed in the upper member 100 and a long lower through-hole 230 formed in the lower member 200 for effective bone fusion with the upper vertebra 1 and the lower vertebra 2 after insertion. Here, the size, shape and location of the upper through-hole 130 and the lower through-hole 230 may be variously designed.

The expandable cage 600 may be formed from materials that are non-harmful for the human body and can withstand impacts and loads applied to the spine for a long time, for example, any one selected from metals such as titanium and carbon alloys, ceramics or plastics (polyether ether ketone (PEEK)), and each element may be formed from the same material or may be formed from different materials depending on the function of each element, and thus a variety of materials may be applied if it is possible to achieve the above-described object.

Hereinafter, the sagittal adjustment unit 300 will be described.

Referring to FIGS. 3 and 7 to 10, the sagittal adjustment unit 300 plays a role in adjusting the sagittal balance of the spine, and in this instance, the sagittal balance refers to the spine in an ideal curved shape by adjusting the curve of the sagittal plane of the spine on the sagittal plane of the spine (when viewed from the side).

The sagittal adjustment unit 300 is disposed between the upper member 100 and the lower member 200 to adjust the distance between the upper member 100 and the lower member 200, and in detail, the sagittal adjustment unit 300 is configured to adjust the sagittal balance of the spine by increasing the distance between the upper member 100 and the lower member 200 in parallel relative to each other.

The sagittal adjustment unit 300 may include a height adjustment screw 310, a height adjustment member 320 and a support connection unit 330.

First, describing the height adjustment screw 310, the height adjustment screw 310 is disposed between the upper member 100 and the lower member 200, and as shown, is positioned in the horizontal direction along the lengthwise direction of the upper member 100 and the lower member 200.

The height adjustment screw 310 is formed in a tubular shape having a screw thread on the outer peripheral surface and has a first adjustment hole 311 into which the adjustment instrument 10 (see FIG. 13) is inserted.

The height adjustment screw 310 may have the first adjustment hole 311 having a polygonal cross-sectional shape to rotate with the rotation of the adjustment instrument 10 inserted therein. In the drawing, the first adjustment hole 311 has a hexagonal cross-sectional shape, and the adjustment instrument 10 may be applied to conform to the cross-sectional shape of the first adjustment hole 311.

Figure 13:
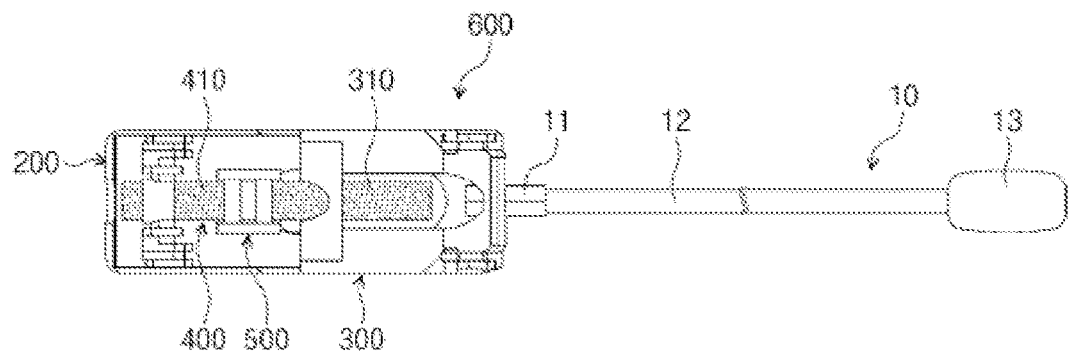
FIGS. 13 to 18 are diagrams showing a process of performing sagittal adjustment and coronal adjustment of the spine by inserting an adjustment instrument into a sagittal adjustment unit in an expandable lumbar cage according to an embodiment of the present disclosure.

Here, the adjustment instrument 10 may include a hexagonal head 11 formed in a set length and a hexagonal cross-sectional shape corresponding to the cross-sectional shape of the first adjustment hole 311, a cylindrical rod 12 connected to the hexagonal head 11 and having a circular cross-sectional shape and a smaller cross-sectional diameter than the cross-sectional diameter of the hexagonal head, and a handle 13 that the user can hold (see FIG. 13). In this instance, the hexagonal head 11 may be formed having the length in the range of 8-12 mm, taking into account the insertion depth into the first adjustment hole 311, but is not limited thereto, and the length may be variously set, considering the simultaneous rotation of the height adjustment screw 310 and a slope adjustment screw 410 described below, into which a second adjustment hole 411 of the slope adjustment screw 410 and the first adjustment hole 311 are simultaneously inserted.

The height adjustment screw 310 moves the height adjustment member 320 by rotation, and thus the movement distance of the height adjustment member 320 is determined according to the thread pitch, and in this instance, the movement distance determines the distance between the upper member 100 and the lower member 200. Accordingly, the pitch of the screw thread of the height adjustment screw 310 may be set according to the adjustment range of the distance between the upper member 100 and the lower member 200. Further, the height adjustment screw 310 supports and maintains the distance between the upper member 100 and the lower member 200 by screw-coupling with the height adjustment member 320, and the pitch and shape of the screw thread may be variously set, taking the coupling into account.

Hereinafter, the height adjustment member 320 will be described.

The height adjustment member 320 is screw-coupled to the height adjustment screw 310 to make a reciprocating movement along the height adjustment screw 310 with the rotation of the height adjustment screw 310, and the height adjustment member 320 plays a role in expanding the expandable cage 600 in the vertical direction on the sagittal plane by increasing the distance between the upper member 100 and the lower member 200 by movement.

In detail, the top of the height adjustment member 320 comes into contact with the lower surface of the upper member 100 and the bottom comes into contact with the upper surface of the lower member 200, and the height adjustment member 320 is configured to move up and down the upper member 100 and the lower member 200 by traction along a tapered sliding surface during movement.

The height adjustment member 320 may include an adjustment unit 321, the support unit 323 and a connection unit 322.

The adjustment unit 321 is screw-coupled to the height adjustment screw 310 through a screw coupling hole 3213, and is configured to move by the rotation of the height adjustment screw 310. The height adjustment screw 310 is constrained such that the location is fixed by the guide unit 500, while the adjustment unit 321 is moveably configured to move with the rotation of the height adjustment screw 310.

Meanwhile, the top of the adjustment unit 321 comes into contact with the lower surface of the upper member 100 and the bottom comes into contact with the upper surface of the lower member 200, and in this instance, the contact is made by the tapered sliding surface, and the adjustment unit 321 may be configured to move up and down the upper member 100 and the lower member 200 along the sliding surface with the movement, thereby reducing or expanding the distance between the upper member 100 and the lower member 200.

In detail, the adjustment unit 321 may have a first sliding surface 3211 and a second sliding surface 3212. The first sliding surface 3211 is formed with inclination on one side of the upper surface of the adjustment unit 321 and comes into contact with an upper slope surface 110 formed on the lower surface of the upper member 100, and is configured to move in sliding contact along the upper slope surface 110 during movement.

The second sliding surface 3212 is symmetrically formed with the first sliding surface 3211 in the vertical direction, and is formed with inclination on one side of the lower surface of the adjustment unit 321 and comes into contact with a lower slope surface 210 formed on the upper surface of the lower member 200, and is configured to make a sliding movement along the lower slope surface 210 during movement.

Meanwhile, the adjustment unit 321 is preferably formed such that each of the first sliding surface 3211 and the second sliding surface 3212 has the same slope angle with respect to the movement direction. This is to ease the sagittal balance adjustment between the upper vertebra 1 and the lower vertebra 2 by symmetrically reducing and expanding the distance between the upper member 100 and the lower member 200.

However, this is an embodiment, and it is possible to change the vertical spacing ratio of the upper member 100 and the lower member 200 for the same screw pitch by changing the slope angle of the first sliding surface 3211 and the second sliding surface 3212. The slope angle of the first sliding surface 3211 may be higher than the slope angle of the second sliding surface 3212 to increase the upward movement rate of the upper member 100 higher than the lower member 200 during the rotation of the height adjustment screw 310. Accordingly, when the expandable cage 600 is inserted into the implantation space, even if the expandable cage 600 is positioned closer to the lower vertebra 2, not at the center of the implantation space, the contact time of the upper vertebra 1 and the lower vertebra 2 for the same screw pitch may be the same due to the high expansion ratio of the upper member 100 by the screw rotation.

The adjustment unit 321 may be configured such that the first sliding surface 3211 and the second sliding surface 3212 are symmetrically disposed in the vertical direction and become narrower as it goes inward (left side in the drawing). In this case, the adjustment unit 321 may be configured to expand the height of the expandable cage 600 by increasing the distance between the upper member 100 and the lower member 200 as it moves inward.

The support unit 323 is disposed on the other side of the upper member 100 and the lower member 200 to support the upper member 100 and the lower member 200.

In the drawing, the support unit 323 has the first slope support surface 324 and the second slope support surface 325 to match the first slope surface 120 of the upper member 100 and the second slope surface 220 of the lower member 200, to prevent interference with the upper member 100 and the lower member 200 during movement.

Further, as shown, the support unit 323 has the first slope support surface 324 and the second slope support surface 325 spaced a set distance apart from the first slope surface 120 and the second slope surface 220 to prevent interference even if the upper member 100 and the lower member 200 expand on one side to form a slope when adjusting the coronal balance.

The support unit 323 may be coaxial with the screw coupling hole 3213, and may have an insertion hole 3231 into which the adjustment instrument 10 is inserted. In this instance, as shown, the insertion hole 3231 preferably has a larger diameter than the diameter of the adjustment instrument 10 to ease the insertion and rotation of the adjustment instrument 10.

The connection unit 322 has one side coupled to the adjustment unit 321 and the other side coupled to the support unit 323, to connect the adjustment unit 321 to the support unit 323. The connection unit 322 may be integrally formed with the support unit 323 and the adjustment unit 321, and as shown, may be formed in a plate shape.

The connection unit 322 may have, at the center, an insertion unit 3221 into which the height adjustment screw 310 is inserted. In this instance, the insertion unit 3221 preferably has a greater width than the diameter of the height adjustment screw 310 to prevent interference caused by the rotation of the height adjustment screw 310, and may have the same width as the diameter of the insertion hole 3231 of the support unit 323.

Hereinafter, the support connection unit 330 will be described.

The support connection unit 330 may have one side connected to the height adjustment member 320, and the other side connected to each of the upper member 100 and the lower member 200 to support the height adjustment member 320, and the support connection unit 330 may have one side connected to the support unit 323 to support the outer end of the height adjustment member 320.

The support connection unit 330 may include a connection axis 331, a first support link 332 and a second support link 333.

First, a pair of connection axes 331 is provided and each is coaxial with respect to the horizontal direction, and the pair of connection axes 331 is each fixed and coupled to two outer sides (in the drawing, front and rear sides) of the support unit 323.

The first support link 332 has one side pivotably coupled to the connection axis 331 and the other side pivotably coupled the upper member 100. Here, the first support link 332 may have the other side pivotably coupled to the upper member 100 by an upper pin 3321 coupled to the upper member 100.

The second support link 333 has one side pivotably coupled to the connection axis 331 and the other side pivotably coupled to the lower member 200. In this instance, the second support link 333 may have the other side pivotably coupled to the lower member 200 by a lower pin 3331 coupled to the lower member 200.

Meanwhile, the first support link 332 and the second support link 333 may have a long pin insertion hole 334, to which the upper pin 3321 and the lower pin 3331 are coupled, to compensate for the movement interference (movement distance) that may occur during the movement of the support unit 323.

According to the foregoing description, the sagittal adjustment unit 300 is configured such that when the height adjustment screw 310 rotates, the height adjustment member 320 screw-coupled to the height adjustment screw 310 moves inward along the height adjustment screw 310, and when the height adjustment member 320 moves inward, the distance between the upper member 100 and the lower member 200 increases by the adjustment unit 321, and the expandable cage 600 expands in the vertical direction with respect to the sagittal plane.

Hereinafter, the coronal adjustment unit 400 will be described.

The coronal adjustment unit 400 plays a role in adjusting the coronal balance of the spine, and corrects the coronal imbalance of the spine on the coronal plane of the spine (when viewed from the front) to achieve an ideal coronal plane balance.

The coronal adjustment unit 400 is disposed between the upper member 100 and the lower member 200, and is coupled to one side of each of the upper member 100 and the lower member 200 to move up and down one side of the upper member 100 and the lower member 200, thereby adjusting the horizontal direction (lengthwise direction) slope of the upper member 100 and the lower member 200 to adjust the coronal balance of the spine.

The coronal adjustment unit 400 may include the slope adjustment screw 410, a movement member 420 and a slope adjustment unit 430.

First, the slope adjustment screw 410 may be positioned in the horizontal direction between the upper member 100 and the lower member 200 and may be formed in a tubular shape having a screw thread formed on the outer peripheral surface and the second adjustment hole 411 into which the adjustment instrument 10 is inserted, and the slope adjustment screw 410 may be configured to rotate with the rotation of the adjustment instrument 10.

The slope adjustment screw 410 has the second adjustment hole 411 having the same diameter and cross-sectional shape as the first adjustment hole 311, and is preferably aligned with the height adjustment screw 310 so that the first adjustment hole 311 and the second adjustment hole 411 are coaxially arranged. The slope adjustment screw 410 is configured to be rotated by the same adjustment instrument 10 which rotates the height adjustment screw 310, to simultaneously rotate the slope adjustment screw 410 and the height adjustment screw 310 or selectively rotate any one of the slope adjustment screw 410 and the height adjustment screw 310 according to the insertion depth of the adjustment instrument 10 when adjusting the sagittal balance and the coronal balance, thereby adjusting the sagittal balance and the coronal balance more easily.

Meanwhile, since the slope adjustment screw 410 and the height adjustment screw 310 are configured to be rotated by the rotation of the same adjustment instrument 10, the screw threads formed on the outer peripheral surface of the height adjustment screw 310 and the slope adjustment screw 410 are preferably formed in the opposite directions. This is to allow the height adjustment member 320 and the movement member 420 to symmetrically move for one direction rotation of the adjustment instrument 10.

That is, the slope adjustment screw 410 and the height adjustment screw 310 having the screw threads of different directions are configured to rotate in different directions when rotated by the same adjustment screw, so that the height adjustment member 320 and the movement member 420 screw-coupled to the slope adjustment screw 410 and the height adjustment screw 310 symmetrically move in the inward direction and the outward direction, respectively. Even if the adjustment instrument 10 simultaneously rotates the slope adjustment screw 410 and the height adjustment screw 310, the height adjustment member 320 and the movement member 420 perform the same expansion or reduction operation.

The movement member 420 has a tubular shape into which the slope adjustment screw 410 is inserted. The movement member 420 has the screw thread on the inner peripheral surface, is screw-coupled to the slope adjustment screw 410, and is configured to make a reciprocating movement along the slope adjustment screw 410 with the rotation of the slope adjustment screw 410.

The slope adjustment unit 430 has one side connected to the movement member 420, and the other side connected to each of the upper member 100 and the lower member 200 to support the slope adjustment screw 410, and plays a role in expanding one side of the expandable cage 600 by moving up and down one side of the upper member 100 and the lower member 200 with the movement of the movement member 420.

The slope adjustment unit 430 may include a pivot axis 431, an upper link 432 and a lower link 433.

First, a pair of pivot axes 431 is provided and each is coaxial with respect to the horizontal direction, and the pair of pivot axes 431 is each fixed and coupled to two outer sides of the movement member 420.

The upper link 432 has one side pivotably coupled to the pivot axis 431 and the other side pivotably coupled to one side of the upper member 100.

The lower link 433 has one side pivotably coupled to the pivot axis 431 and the other side pivotably coupled to one side of the lower member 200.

According to the foregoing description, the coronal adjustment unit 400 is configured such that when the slope adjustment screw 410 rotates, the movement member 420 screw-coupled to the slope adjustment screw 410 moves inward along the slope adjustment screw 410, and subsequently, when the movement member 420 moves inward, the distance between one side of the upper member 100 and one side of the lower member 200 increases by the slope adjustment unit 430, and one side of the expandable cage 600 expands with respect to the coronal plane.

Meanwhile, the expandable cage 600 may further include a guide unit 500 between the upper member 100 and the lower member 200. The guide unit 500 is where an end of the height adjustment screw 310 and an end of the slope adjustment screw 410 disposed opposite the end of the height adjustment screw 310 are seated to guide the height adjustment screw 310 and the slope adjustment screw 410.

In detail, the guide unit 500 may include a seating unit 510 in which the end of each of the height adjustment screw 310 and the slope adjustment screw 410 is seated.

Figure 11:
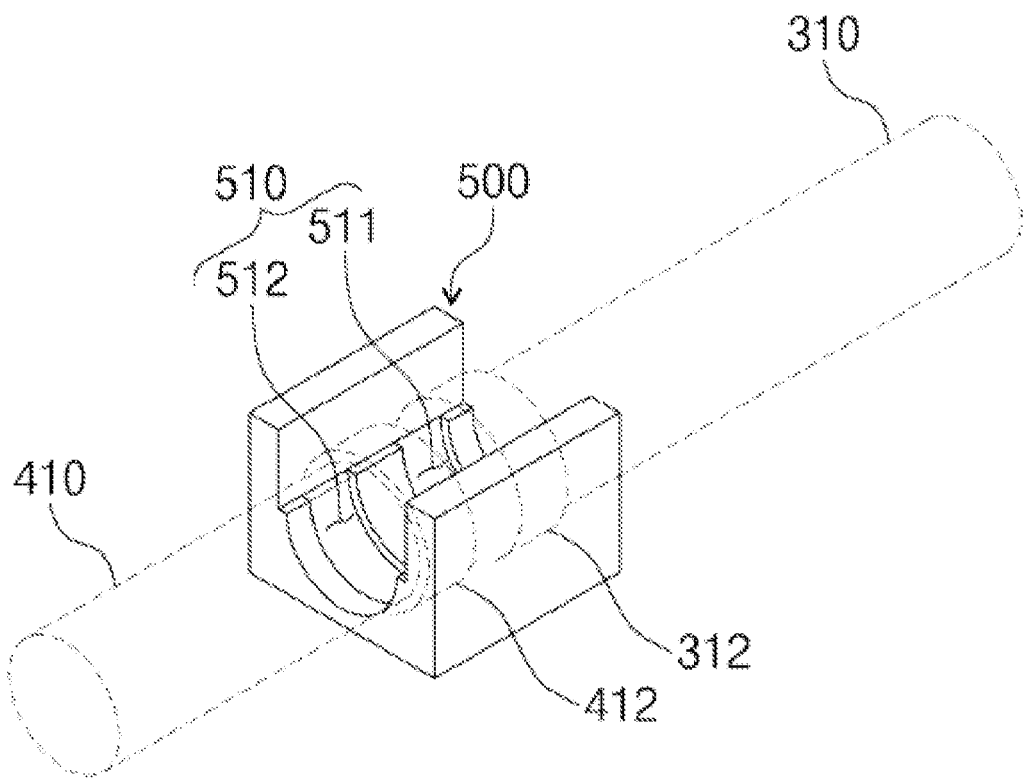
FIG. 11 is a perspective view showing a guide unit of the expandable lumbar cage of FIG. 3.

Referring to FIG. 11, the seating unit 510 is where the height adjustment screw 310 and the slope adjustment screw 410 are seated to support them so that their locations are fixed, and the height adjustment screw 310 and the slope adjustment screw 410 are rotatably seated in the seating unit 510 such that the height adjustment screw 310 and the slope adjustment screw 410 are allowed to rotate, but held in fixed locations.

Describing the detailed configuration, first, the height adjustment screw 310 may have a first flange 312 at the end where the height adjustment screw 310 is seated in the guide unit 500, and the slope adjustment screw 410 may have a second flange 412 at the end where the slope adjustment screw 410 is seated in the guide unit 500.

The seating unit 510 may have a seating groove in which each of the first flange 312 and the second flange 412 is seated. Here, the seating groove may include a first flange groove 511 in which the first flange 312 is seated and rotatably fitted, and a second flange groove 512 in which the second flange 412 is seated and rotatably fitted.

According to the foregoing description, the expandable cage 600 according to an embodiment of the present disclosure may adjust not only the sagittal balance but also the coronal balance using only one configuration, effectively treat compound spinal deformity using the minimum number of cages, and achieve the sagittal balance and the coronal balance by the user's simple manipulation, thereby improving the usability.

Hereinafter, a method for inserting the expandable cage 600 according to an embodiment of the present disclosure will be described. Here, the expandable cage 600 is the same as the above-described expandable lumbar cage and its detailed description is omitted herein, and hereinafter, the method for inserting the expandable cage 600 will be described in detail.

Figure 12:
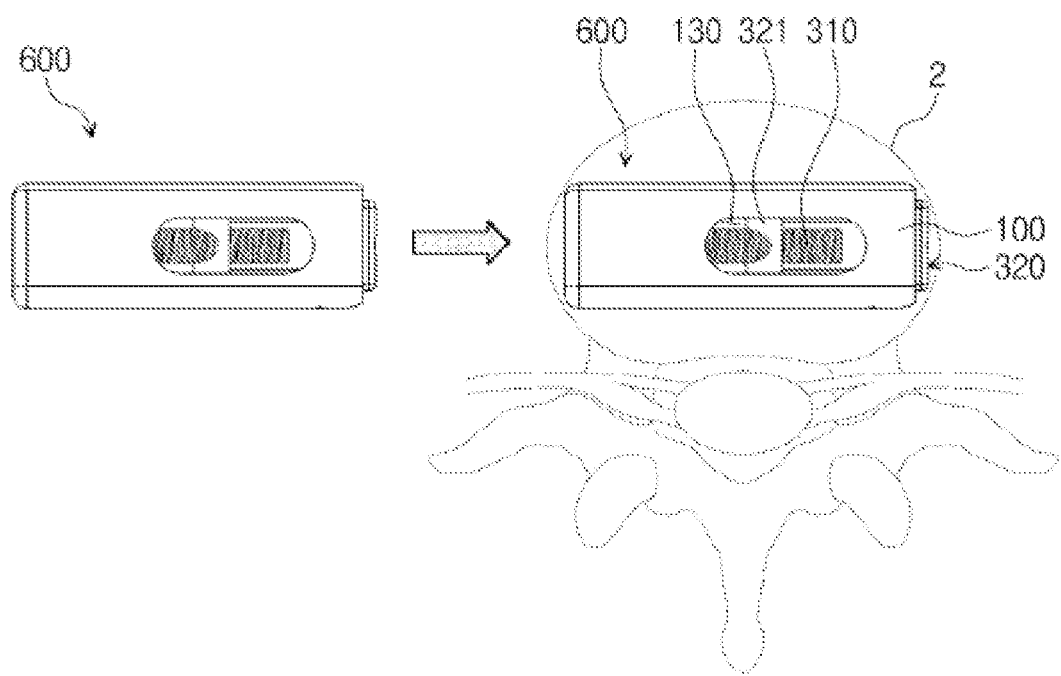
FIG. 12 is a plan view showing a method for inserting an expandable lumbar cage according to an embodiment of the present disclosure.

First, as shown in FIG. 12, the expandable cage 600 of the present disclosure is inserted into the implantation space between the upper vertebra 1 and the lower vertebra 2 by the lateral approach of the spine, or although not shown, the anterolateral approach of the spine. Accordingly, as opposed to the conventional posterior insertion of the spinal cage, the method for inserting the expandable cage 600 of the present disclosure may bypass the major blood vessels of the human body, and there is no risk of damage to the muscles or ligaments, thereby ensuring safer surgery.

Meanwhile, as described above, the expandable cage 600 of the present disclosure may allow the insertion of the adjustment instrument 10 from either side, i.e., one side where the height adjustment screw 310 is positioned, and the other side where the slope adjustment screw 410 is positioned, thereby achieving the coronal adjustment and sagittal adjustment.

Hereinafter, a method for performing the coronal adjustment and sagittal adjustment by inserting the adjustment instrument 10 into the sagittal adjustment unit 300 on one side, and a method for performing the coronal adjustment and sagittal adjustment by inserting the adjustment instrument 10 into the coronal adjustment unit 400 on the other side will be described.

First, the method for performing the coronal adjustment and sagittal adjustment by inserting the adjustment instrument 10 using the sagittal adjustment unit 300 will be described.

First, the expandable cage 600 of the present disclosure is inserted in the lateral position or anterolateral position of the spine, and the insertion may be performed by an insertion instrument (not shown) for effective insertion. The insertion instrument may include a distractor and a slide. Here, the distractor plays a role in widening the implantation space and keeping the space wide to allow the expandable cage 600 to enter. Additionally, the slide plays a role in inserting the expandable cage 600 into the implantation space widened by the distractor, with the top and bottom of the expandable cage 600 covered therewith.

Using the insertion instrument, the user inserts the expandable cage 600 in a non-expanded state into the implantation space.

In this instance, as described above, the expandable cage 600 has the upper surface of the upper member 100 and the lower surface of the lower member 200 formed with inclination such that the height of one side (anterior) is higher than the height of the other side (posterior) with respect to the sagittal plane.

When inserting the expandable cage 600 into the implantation space, the user inserts the expandable cage 600 into the implantation space such that a higher side of the expandable cage 600 faces the anterior portion of the spine.

After the expandable cage 600 is inserted into the implantation space as described above, the sagittal balance and the coronal balance are adjusted according to the subject's spine condition.

First, the sagittal balance of the spine is adjusted by expanding the distance between the upper member 100 and the lower member 200 with respect to the sagittal plane of the spine through the sagittal adjustment unit 300.

Figure 14:
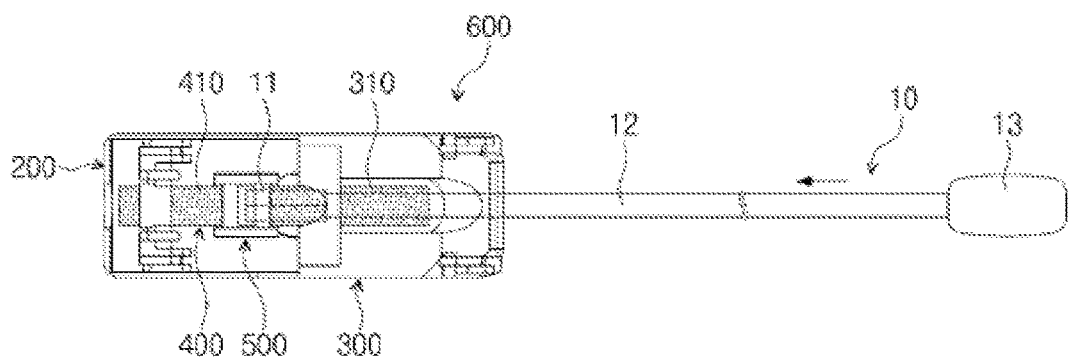
Figure 15:
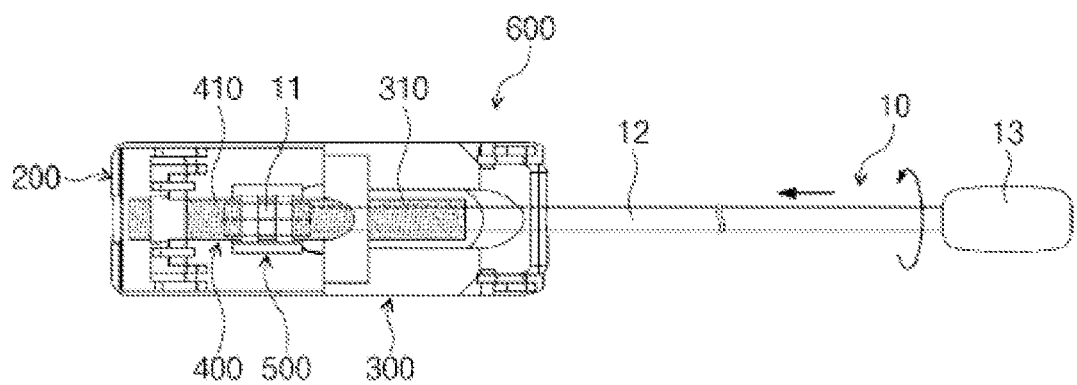

To this end, as shown in FIGS. 13 to 15, first, the user inserts the adjustment instrument 10 such that the hexagonal head 11 is coupled to the first adjustment hole 311 of the height adjustment screw 310 and the second adjustment hole 411 of the slope adjustment screw 410.

Figure 16:
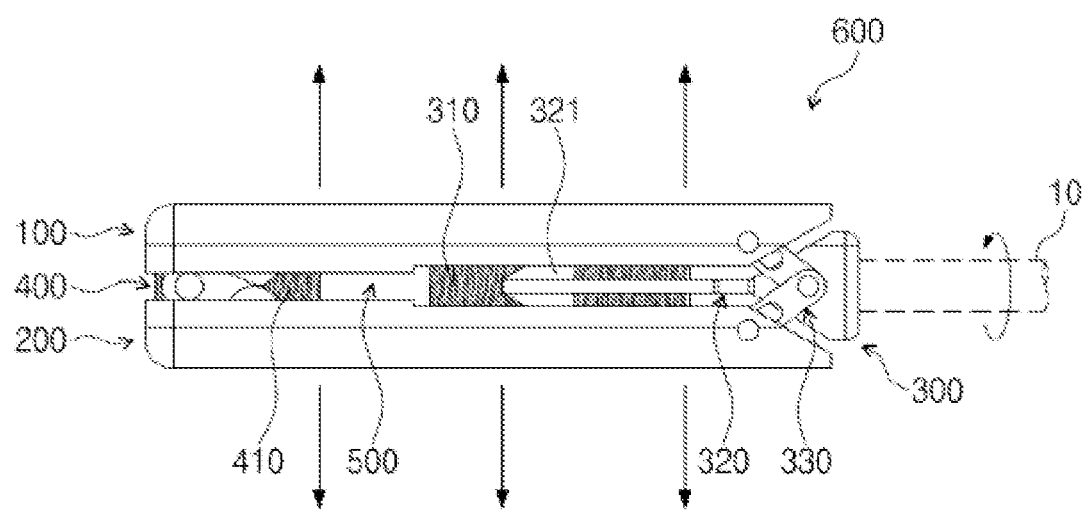

Subsequently, as shown in FIG. 16, in this state, the user rotates the adjustment instrument 10 to simultaneously rotate the height adjustment screw 310 and the slope adjustment screw 410 and expand the distance between the upper member 100 and the lower member 200, thereby adjusting the sagittal balance.

Meanwhile, in this instance, the user inserts the hexagonal head 11 of the adjustment instrument 10 into both the first adjustment hole 311 and the second adjustment hole 411 to adjust the sagittal balance, but this is a preferred embodiment, and the sagittal balance may be adjusted by inserting and coupling the hexagonal head 11 to only the first adjustment hole 311 and rotating the height adjustment screw 310.

When the height adjustment screw 310 rotates the slope adjustment screw 410 as described above and a set expansion range is reached, the user completes the sagittal balance adjustment by stopping the rotation of the adjustment instrument 10.

When the sagittal balance adjustment is completed, the user adjusts the coronal balance of the spine by expanding such that one side of the upper member 100 and the lower member 200 is inclined with respect to the coronal plane of the spine through the coronal adjustment unit 400.

Figure 17:
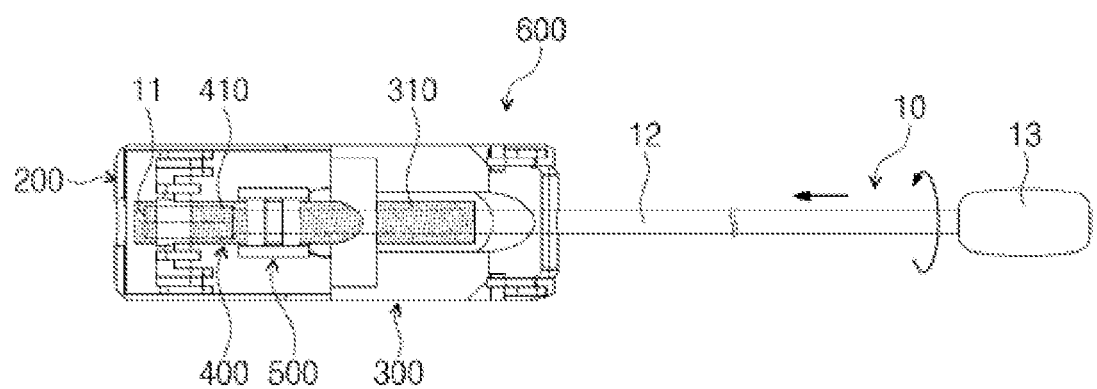

To this end, as shown in FIG. 17, to rotate only the slope adjustment screw 410, the user further advances the adjustment instrument 10 in the insertion direction so that the hexagonal head 11 is inserted and coupled to only the second adjustment hole 411, and in this state, expands by rotating the adjustment instrument 10 to rotate the slope adjustment screw 410 according the set expansion range.

Figure 18:
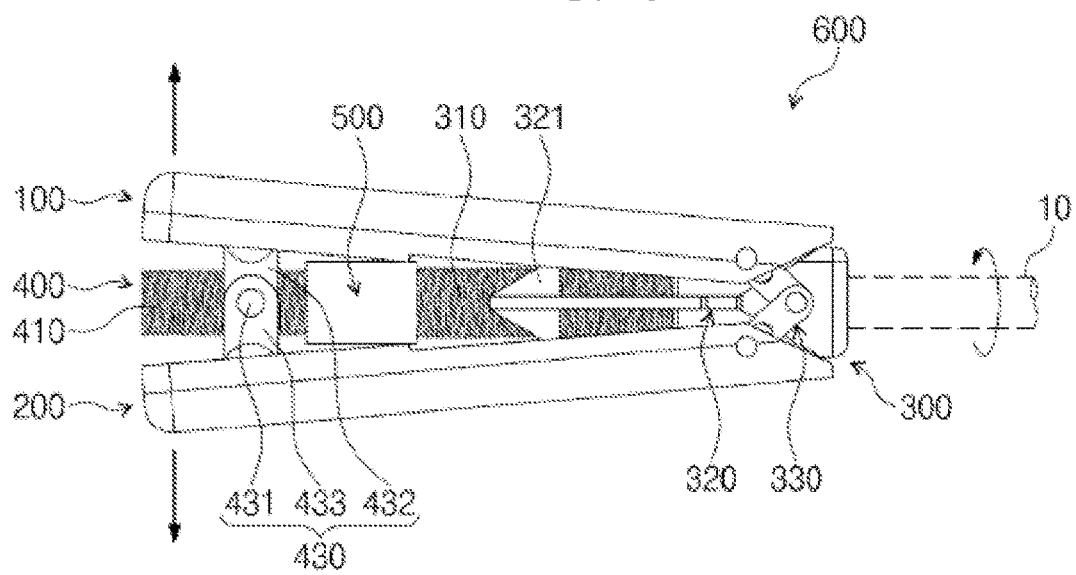

FIG. 18 is a diagram showing that the user rotated only the slope adjustment screw 410, and as shown, one side of the expandable cage 600 expands, and through this, the coronal balance of the spine may be adjusted.

Subsequently, the method for performing the coronal adjustment and the sagittal adjustment by inserting the adjustment instrument 10 into the coronal adjustment unit 400 will be described with reference to FIGS. 19 to 23.

Figure 19:
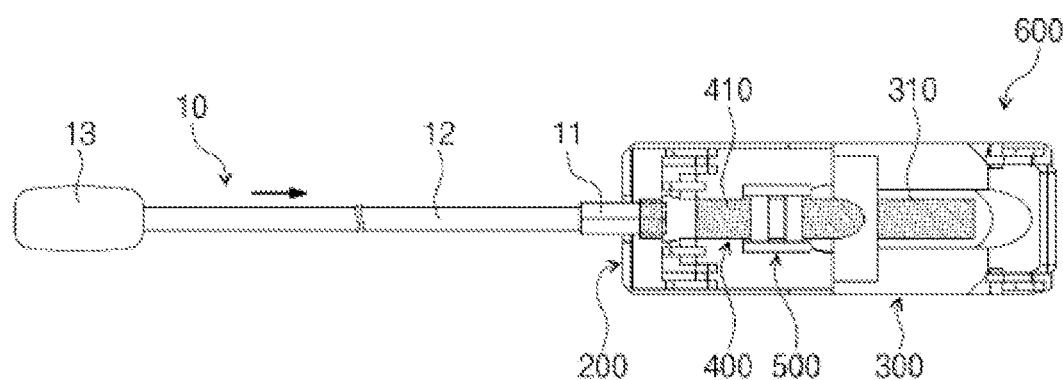
FIGS. 19 to 23 are diagrams showing a process of performing sagittal adjustment and coronal adjustment of the spine by inserting an adjustment instrument into a coronal adjustment unit in an expandable lumbar cage according to an embodiment of the present disclosure.
Figure 20:
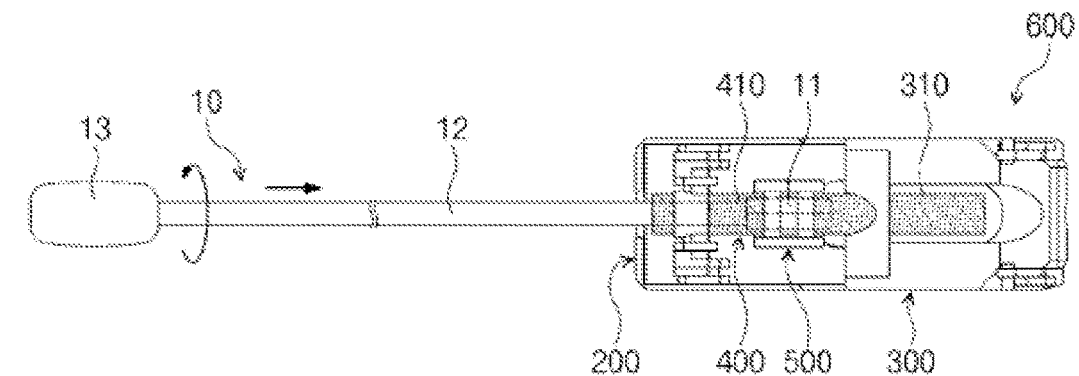

In this case, as opposed to the foregoing description, as shown in FIGS. 19 and 20, the user inserts the adjustment instrument 10 in the direction of the slope adjustment screw 410 such that the hexagonal head 11 is coupled to the first adjustment hole 311 of the height adjustment screw 310 and the second adjustment hole 411 of the slope adjustment screw 410.

Figure 21:
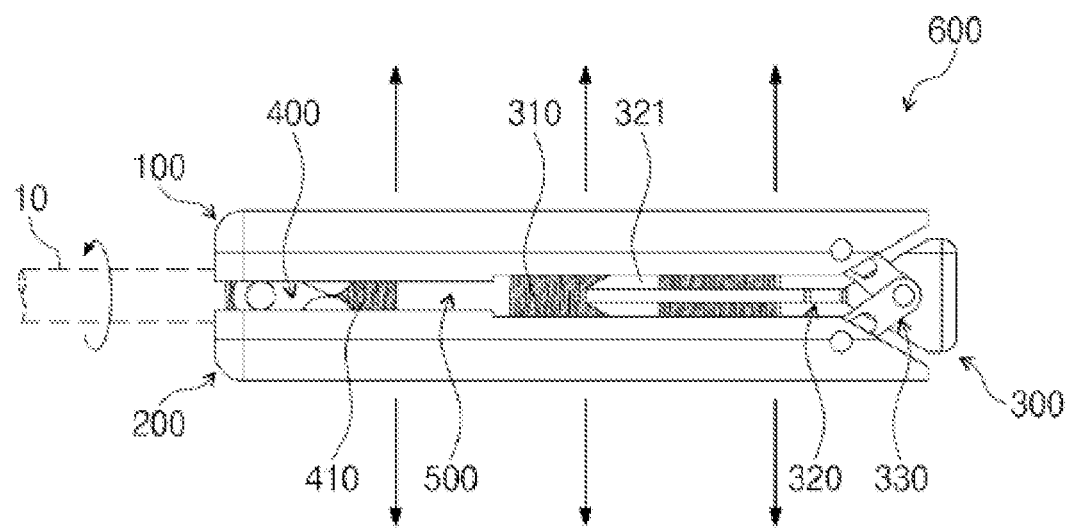

Subsequently, as shown in FIG. 21, in this state, the user rotates the adjustment instrument 10 to simultaneously rotate the height adjustment screw 310 and the slope adjustment screw 410 and expand the distance between the upper member 100 and the lower member 200, thereby adjusting the sagittal balance.

Figure 22:
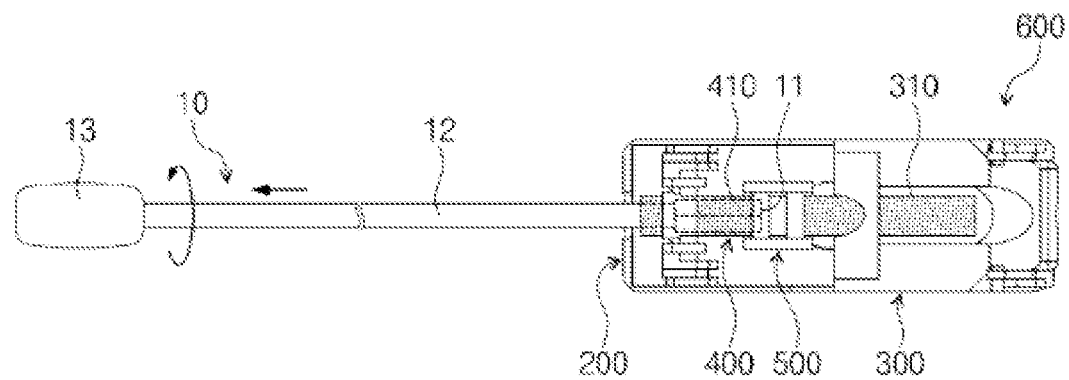

When the sagittal balance adjustment is completed, as shown in FIG. 22, to adjust the coronal balance, the user retreats the adjustment instrument 10 in the opposite direction to the insertion direction so that the hexagonal head 11 is inserted and coupled to only the second adjustment hole 411, and then rotates the adjustment instrument 10.

Figure 23:
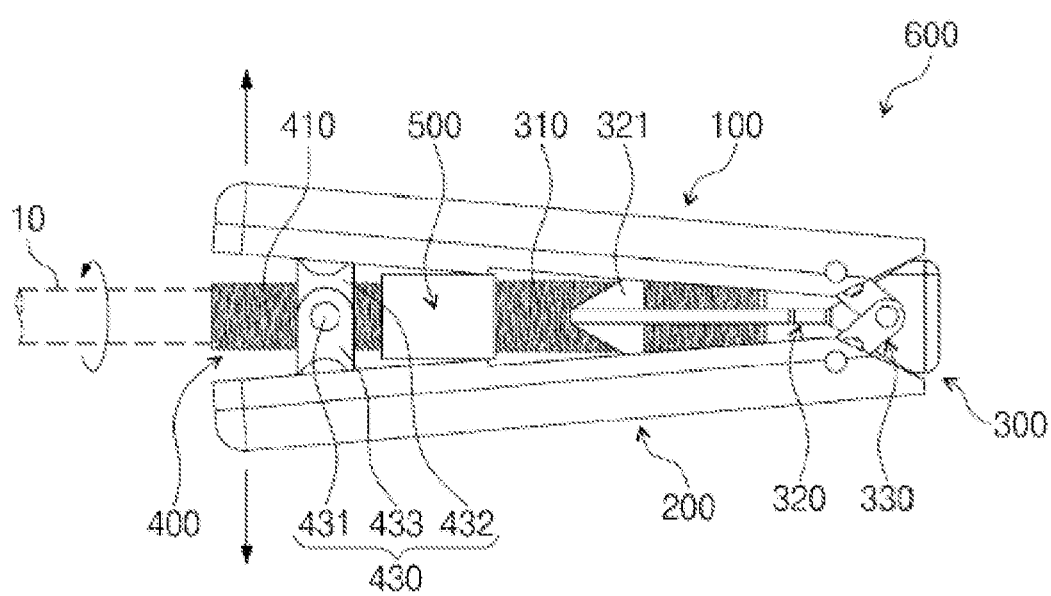

Accordingly, as shown in FIG. 23, the expandable cage 600 expands with inclination on one side, and the coronal balance of the spine may be adjusted.

According to the foregoing description, the user may easily adjust the sagittal balance and the coronal balance by adjusting only the insertion depth of the adjustment instrument 10 and rotating the height adjustment screw 310 and the slope adjustment screw 410, without needing to replace and re-insert the adjustment instrument 10 to adjust the sagittal balance and the coronal balance.

Additionally, the expandable cage 600 according to the present disclosure may be inserted in both the left direction and the right direction, considering the lateral or anterolateral insertion, and it is possible to selectively expand the left side or the right side of the spine after insertion by changing the anterior-posterior direction of the coronal adjustment unit 400 with respect to the insertion direction.

In other words, when in the subject's spine of the surgical range, the upper level is compressed on the left side and the lower level is compressed on the right side, so it is necessary to expand the left side of the upper level and the right side of the lower level, the present disclosure does need to cut both the left side and the right side and cuts only one side, and inserts the expandable cage 600 by changing the anterior-posterior direction depending on the expansion location through the incision site and expands it.

In case that it is necessary to cut the subject's left side (ipsilateral side) and expand the left side of the spine when the subject is viewed from the front, the user adjusts the anterior-posterior direction of the expandable cage 600 to place the coronal adjustment unit 400 close to the incision site, and inserts into the implantation space through the insertion instrument. In contrast, to expand the right side of the spine with the subject's left side being cut, the user adjusts the anterior-posterior direction of the expandable cage 600 to place the coronal adjustment unit 400 in the anterior side far from the incision site, and in this state, inserts into the implantation space through the insertion instrument.

As described above, the method for inserting the expandable cage 600 of the present disclosure may adjust the coronal balance by selectively expanding the left side or the right side of the spine by changing the direction of the coronal adjustment unit 400 depending on the subject's spine condition, and expand both the left side and the right side of the spine by cutting only one side, thereby minimizing the incision.

According to the foregoing description, the method for inserting the expandable cage 600 according to an embodiment of the present disclosure may insert the expandable cage 600 in a non-expanded state into the lateral position or anterolateral position of the spine through the insertion instrument, after the insertion, rotate the height adjustment screw 310 through the adjustment instrument 10 to expand the distance between the upper member 100 and the lower member 200 for primary expansion (horizontal expansion) of the expandable cage 600, thereby adjusting the sagittal balance, and after the sagittal balance adjustment, change the insertion depth of the adjustment instrument 10 and rotate the slope adjustment screw 410 to expand one side of the expandable cage 600 for secondary expansion of the expandable cage 600, thereby adjusting the coronal balance.

While the present disclosure has been hereinabove described with reference to the embodiments shown in the drawings, this is provided for illustration purposes only and it will be appreciated by those skilled in the art that various modifications and variations may be made thereto. Therefore, the true technical protection scope of the present disclosure should be defined by the technical spirit of the appended claims.

[DETAILED DESCRIPTION OF MAIN ELEMENTS]

| | |
|---|---|
| 10: Adjustment instrument | 100: Upper member |
| 110: Upper slope surface | 120: First slope surface |
| 130: Upper through-hole | 200: Lower member |
| 210: Lower slope surface | 220: Second slope surface |
| 230: Lower through-hole | 300: Sagittal adjustment unit |
| 310: Height adjustment screw | 311: First adjustment hole |
| 312: First flange | 320: Height adjustment member |
| 321: Adjustment unit | 3211: First sliding surface |
| 3212: Second sliding surface | 3213: Screw coupling hole |
| 322: Connection unit | 3221: Insertion unit |
| 323: Support unit | 3231: Insertion hole |
| 324: First slope support surface | 325: Second slope support surface |
| 330: Support connection unit | 331: Connection axis |
| 332: First support link | 3321: Upper pin |
| 333: Second support link | 3331: Lower pin |
| 334: Pin insertion hole | 400: Coronal adjustment unit |
| 410: Slope adjustment screw | 411: Second adjustment hole |
| 412: Second flange | 420: Movement member |
| 430: Slope adjustment unit | 431: Pivot axis |
| 432: Upper link | 433: Lower link |
| 500: Guide unit | 510: Seating unit |
| 511: First seating groove | 512: Second seating groove |
| 600: Expandable cage | |

The invention claimed is:

1. An expandable lumbar cage, comprising:
an upper member;
a lower member spaced apart below the upper member;
a sagittal adjustment unit disposed between the upper member and the lower member and coupled to a first portion of each of the upper member and the lower member and configured to adjust a distance between the upper member and the lower member, thereby adjusting sagittal balance of a spine, wherein the sagittal adjustment unit comprises a height adjustment screw positioned along a lengthwise direction with respect to the upper member and the lower member and having a screw thread on an outer peripheral surface thereof, wherein the height adjustment screw is configured to receive an adjustment instrument and rotate with rotation of the adjustment instrument;
a coronal adjustment unit disposed between the upper member and the lower member and coupled to a second portion of each of the upper member and the lower member, and configured to raise and lower the second portion of each of the upper member and the lower member to adjust inclination of the upper member and the lower member, thereby adjusting coronal balance of the spine, wherein the coronal adjustment unit comprises a slope adjustment screw positioned along the lengthwise direction with respect to the upper member and the lower member and coaxial with the height adjustment screw and having a screw thread on an outer peripheral surface thereof, wherein the adjustment instrument is configured to be inserted into the slope adjustment screw, and the slope adjustment screw rotates with rotation of the adjustment instrument; and
a guide unit disposed between the upper member and the lower member, and including a seating unit in which an end of the height adjustment screw and an end of the slope adjustment screw disposed opposite the end of the height adjustment screw are seated, to guide the height adjustment screw and the slope adjustment screw.

2. The expandable lumbar cage according to claim 1, wherein the upper member has a rectangular shape and a downwardly sloping upper surface with respect to a sagittal plane of the spine.

3. The expandable lumbar cage according to claim 2, wherein the lower member has a rectangular shape corresponding to the shape of the upper member and an upwardly sloping lower surface with respect to the sagittal plane of the spine.

4. The expandable lumbar cage according to claim 1, wherein the sagittal adjustment unit further comprises:
   a height adjustment member screw-coupled to the height adjustment screw to move with the rotation of the height adjustment screw, wherein a top of the height adjustment member is in contact with a lower surface of the upper member and a bottom of the height adjustment member is in contact with an upper surface of the lower member, and wherein the height adjustment member is moved to adjusts the distance between the upper member and the lower member by the rotation of the height adjustment screw; and
   a support connection unit with a first side thereof connected to the height adjustment member and a second side thereof connected to each of the upper member and the lower member to support the height adjustment member.

5. The expandable lumbar cage according to claim 4, wherein the coronal adjustment unit further comprises:
   a movement member having a tubular shape and having a screw thread on an inner peripheral surface thereof into which the slope adjustment screw is screw-coupled, wherein the movement member moves with the rotation of the slope adjustment screw; and
   a slope adjustment unit having a first side thereof connected to the movement member, and a second side thereof connected to each of the upper member and the lower member, to raise or lower the second portion of the upper member and the lower member with the movement of the movement member.

6. The expandable lumbar cage according to claim 5, wherein the slope adjustment unit comprises:
   a pivot axis extending through the movement member;
   an upper link having a first side thereof pivotably coupled about the pivot axis to the movement member and a second side thereof coupled to the upper member; and
   a lower link having a first side thereof pivotably coupled about the pivot axis to the movement member and a second side thereof coupled to the one side of the lower member.

7. The expandable lumbar cage according to claim 5, wherein the height adjustment screw, into which the adjustment instrument is configured to be inserted, rotates by the rotation of the adjustment instrument and has a first adjustment hole having a polygonal cross-sectional shape, and
   wherein the slope adjustment screw, into which the adjustment instrument is configured to be inserted, rotates by the rotation of the adjustment instrument and has a second adjustment hole having a same diameter and cross-sectional shape as the first adjustment hole.

8. The expandable lumbar cage according to claim 7, wherein the height adjustment screw and the slope adjustment screw are aligned and the first adjustment hole and the second adjustment hole are coaxially arranged, and wherein the adjustment instrument is configured to rotate at least one of the height adjustment screw or the slope adjustment screw according to an insertion depth of the adjustment instrument.

9. The expandable lumbar cage according to claim 4, wherein the sagittal adjustment unit further comprises:
   an adjustment unit configured to move by the rotation of the height adjustment screw screw-coupled to the adjustment unit through a screw coupling hole, wherein a top of the adjustment unit is in contact with the lower surface of the upper member and a bottom of the adjustment unit is in contact with the upper surface of the lower member, and wherein the adjustment unit raises and lowers the upper member and the lower member with the movement of the adjustment unit;
   a support unit configured to engage each of the upper member and the lower member to support the upper member and the lower member; and
   a connection unit connecting the adjustment unit to the support unit.

10. The expandable lumbar cage according to claim 9, wherein the adjustment unit comprises:
    a first sliding surface having an inclined slope, wherein the first sliding surface comes into contact with an upper slope surface disposed on the lower surface of the upper member, and slides along the upper slope surface during the movement of the adjustment unit; and
    a second sliding surface having an inclined slope, wherein the second sliding surface comes into contact with a lower slope surface disposed on the upper surface of the lower member, and slides along the lower slope surface during the movement of the adjustment unit, and
    wherein the adjustment unit raises and lowers the upper member and the lower member along the first sliding surface and the second sliding surface with the movement of the adjustment unit, to reduce or expand the distance between the upper member and the lower member.

11. The expandable lumbar cage according to claim 10, wherein the first sliding surface and the second sliding surface have a same slope angle with respect to a movement direction.

12. The expandable lumbar cage according to claim 11, wherein
    the first sliding surface and the second sliding surface are symmetrically disposed in a vertical direction and each have a decreasing thickness, and wherein the adjustment unit is configured to expand the distance between the upper member and the lower member as the adjustment unit moves toward the second portion of each of the upper member and the lower member.

13. The expandable lumbar cage according to claim 9, wherein the upper member has a first slope surface upwardly sloping outwards on a lower surface of the first portion of the upper member,
    wherein the lower member has a second slope surface downwardly sloping on an upper surface of the second portion of the lower member, opposite the first slope surface, and
    wherein the support unit has a first slope support surface corresponding to the first slope surface and a second slope support surface corresponding to the second slope surface.

14. The expandable lumbar cage according to claim 9, wherein the support unit has an insertion hole into which the adjustment instrument is configured to be inserted, and the insertion hole is coaxial with the screw coupling hole.

15. The expandable lumbar cage according to claim 9, wherein the support connection unit comprises:
- a connection axis extending through the support unit;
- a first support link having a first side thereof pivotably coupled about the connection axis to the support unit and a second side thereof pivotably coupled to the upper member; and
- a second support link having a first side thereof pivotably coupled about the connection axis to the support unit and a second side thereof pivotably coupled to the lower member.

* * * * *